United States Patent [19]

Gerber

[11] 3,943,125

[45] Mar. 9, 1976

[54] SUBSTITUTED TETRAAMINO HETEROCYCLIC COMPOUNDS, USEFUL IN THE PREPARATION OF SUBSTITUTED POLYBENZIMIDAZOLES AND POLY-IMIDAZOPYRROLONES

[75] Inventor: Arthur H. Gerber, University Hts., Ohio

[73] Assignee: Horizons Incorporated, a division of Horizons Research Incorporated, Cleveland, Ohio

[22] Filed: Jan. 31, 1974

[21] Appl. No.: 438,393

[52] U.S. Cl........ 260/240 D; 260/30.2; 260/30.8 R; 260/32.4; 260/32.6 N; 260/72.5; 260/78.4 R; 260/78.4 E; 260/78 TF; 260/47 CP; 260/65; 260/246 R; 260/250 R; 260/294.8 F; 260/295 CA; 260/296 R; 260/309.2

[51] Int. Cl.[2]............... C07D 213/61; C07D 213/74

[58] Field of Search..................... 260/296 R, 240 D

[56] References Cited
UNITED STATES PATENTS

| | | | |
|---|---|---|---|
| 2,052,633 | 9/1936 | Kranz................................. | 260/576 |
| 3,470,172 | 9/1969 | Kaufman........................... | 260/296 R |
| 3,678,061 | 7/1972 | Coburn.............................. | 260/296 R |
| 3,740,410 | 6/1973 | Gerber............................... | 260/295 S |
| 3,804,804 | 4/1974 | Gerber et al...................... | 260/47 CP |
| 3,838,154 | 9/1974 | Gerber.............................. | 260/296 R |

OTHER PUBLICATIONS

Bernstein et al., J. Am. Chem. Soc. 69 (1947), p. 1151–1157.

*Primary Examiner*—Arthur P. Demers
*Attorney, Agent, or Firm*—Lawrence I. Field

[57] ABSTRACT

This invention relates to substituted tetraamino pyridines and to methods whereby such compounds are prepared. It also relates to the linear precyclized polymers produced by reaction of substituted tetraaminopyridines, or their acid salts, with a substantially equimolar amount of a suitable bis(acid halide) or dianhydride in a polar aprotic solvent at temperatures between about −10°C and 70°C. The resulting soluble, high molecular weight precyclized intermediates can be cyclodehydrated and may also be crosslinked to yield novel polybenzimidazoles and polyimidazopyrrolones.

6 Claims, No Drawings

SUBSTITUTED TETRAAMINO HETEROCYCLIC COMPOUNDS, USEFUL IN THE PREPARATION OF SUBSTITUTED POLYBENZIMIDAZOLES AND POLY-IMIDAZOPYRROLONES

This invention is an improvement over the inventions described in U.S. Pat. No. 3,740,410 issued June 19, 1973 and U.S. Pat. No. 3,804,804 issued April 16, 1974, the disclosures of which are incorporated herein by this reference.

This invention relates to substituted tetraamino heterocyclic compounds and methods for the preparation of said compounds. These tetraamino compounds are intermediates for the preparation of substituted polybenzimidazoles and polyimidazopyrrolones.

The invention also relates to the preparation of substituted polybenzimidazoles and polyimidazopyrrolones from said tetraamino compounds and to the improved polybenzimidazoles and polyimidazopyrrolones so produced.

One object of the invention is to provide novel substituted tetraamino pyridine compounds and their acid salts, and to react such compounds with a substantially equimolar amount of a suitable bis(acid halide) or dianhydride in a polar aprotic solvent at moderate temperatures (i.e. below 70°C) whereby a soluble, high molecular weight linear precyclized intermediate is produced, and thereafter converting said intermediate to new and useful polybenzimidazoles and polyimidazopyrrolones with exceptional properties, by cyclodehydration or by crosslinking of said intermediates.

The present invention differs from the invention described in my U.S. Pat. No. 3,740,410 issued June 19, 1973, principally in the presence of substituents on the tetraaminopyridine reactant from which the precyclized polymers are obtained.

The monomers of this invention are substituted tetraminopyridines with either an alkyl substituent on a ring position or an alkyl or aryl substituent on one or both of the alpha nitrogens, or by extension via one or more pyridine rings. From these monomers, polybenzimidazoles and polymidazopyrrolones are obtained which are thermally stable and which also exhibit improved solubility in the cyclized uncured state, as compared to the corresponding polybenzimidazoles and polyimidazopyrrolones prepared from the unsubstituted 2,3,5,6-tetraaminopyridine. These properties enhance processability into many useful forms for high temperature applications such as in films, coatings, fibers, adhesive and laminating formulations, as matrices for structural composites, and semi-permeable membranes.

The substituted tetraamino pyridine compounds of this invention are those represented by one of the following formulae:

Formula I

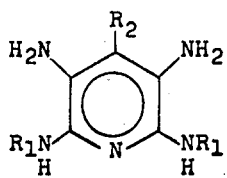

Formula II

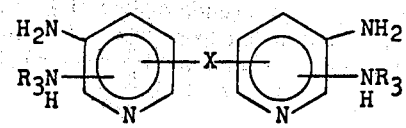

In the above general formulae:

$R_2$ is a monovalent member selected from the group consisting of hydrogen, methyl, ethyl, propyl, butyl and pentyl;

$R_1$ is a monovalent member selected from the group consisting of hydrogen, alkyl, substituted alkyl, alkenyl, substituted alkenyl, arylalkyl, aryl, heteroaryl, heteroarylalkyl, substituted arylalkyl, substituted aryl and substituted heteroaryl, with aryl and heteroaryl including monocyclic, linear bicyclic and fused ring structures, typical substituents within the scope of this invention include: methyl, phenyl, pyridyl, F (aromatic), Cl (aromatic), —CN, —COOH and its salts, —COOC$_6$H$_5$, —SO$_3$H and its salts, —SH, thioaryl, thioalkyl, —CH=CHC$_6$H$_5$, and N,N-(dialkylamino), with the proviso that not all $R_1$ and $R_2$ can be H; and all of the $R_1$'s of Formula I need not be identical;

$R_3$ is a monovalent radical selected from the group consisting of H and alkyl of 1 to 5 carbon atoms and X is zero or a divalent radical selected from alkylene of 1 to 3 carbon atoms, —S—, —O—, and

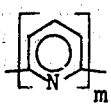

where $m$ is equal to 1 or 2; each R$_3$NH— group is located ortho to an amino group and the pyridyl rings containing the amino groups are joined via the 2,2', 3,3' or 2,3' positions with the proviso that X can equal

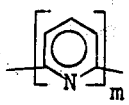

where the pyridyl groups are joined 2,2' and where X equals zero both $R_3$'s cannot be hydrogen when the pyridyl groups are joined 2,2'; and all of the $R_3$'s of Formula II need not be identical.

The nature of $R_1$, $R_2$ and $R_3$ will be apparent from the following list of specific compounds considered representative of those contemplated in the present invention:

2,3,5,6-tetraamino-4-methylpyridine
2,3,5,6-tetraamino-4-ethylpyridine
3,5-diamino-2,6-di(methylamino)pyridine
3,5-diamino-2,6-di(benzylamino)pyridine
3,5-diamino-2,6-di(α-pyridylamino)pyridine    3,5-diamino-2,6-di(anilino)pyridine*
3,5-diamino-2,6-di(m-cyanoanilino)pyridine
3,5-diamino-di(p-mercaptoanilino)-4-methylpyridine
3,5-diamino-2,6-di(p-stilbylamino)pyridine
2,3,5-triamino-6-anilinopyridine 3,5-diamino-4-methyl-2,6-di (p-sulfoanilino)pyridine
3,5-diamino-2,6-di(allylamino)pyridine
5,5'-diamino-4,4'-di(methylamino)-2,2'-bipyridine
di(5-amino-6-ethylamino-2-pyridyl)ether
5',5'',6',6''-tetraamino-2:6-di-2'-pyridylpyridine
3,5-diamino-2,6-di[m-(endo-cis-bicyclo[2.2.1]-5-heptene-2,3-imido)anilino]pyridine. (This compound is 3,5-diamino-2,6-di(anilino)pyridine (above)* in which one meta hydrogen of each anilino substituent has been replaced by a

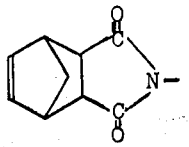

group.

Tetramines with reactive groups such as alkenyl, $-C_6H_4CH=CHC_6H_5$, dialkylamino, cyano,

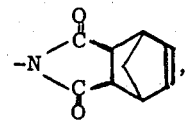

mercapto, carboxylic acid, phenyl carboxylate, and sulfonic acid are preferably used in small amounts as comonomers with other tetramines of this invention, in order to provide functional groups which are desirable for increasing initial polymer solubility or for ultimate crosslinking of polymer.

Compounds of Formula I are somewhat unstable and extremely sensitive to oxidation. They may be stored at subzero temperatures. Because of their instability, they are preferably stored and used as their polyacid salts. Suitable salt forming acids include HCl, HBr, sulfuric, orthophosphoric, alkanesulfonic acids, trifluoromethanesulfonic and trifluoroacetic. Compounds of Formula II are more stable than those of Formula I and can be stored as the free amines or polyacid salts. However, it is also preferred to store them as their acid salts. Tetraamines of Formulae I or II can be regenerated from their acid salts by careful neutralization under anaerobic conditions, preferably below room temperature.

2,3,5,6-tetraaminopyridine trihydrochloride and 4,4',5,5'-tetraamino-2,2'-bipyridine have been described in J. Heterocyclic Chem., 8, 841 (1972), U.S. Pat. No. 3,740,410 issued June 19, 1973 and in British Specification No. 1,115,607. However, these tetramines, when compared to the corresponding tetramines or substituted tetramines of this invention, particularly as their acid salts, are less soluble and more importantly afford polybenzimidazoles and polyimidazopyrrolones of lower solubility and thermal stability, probably because of the presence of not more than one vulnerable ring C-H bond in the residual tetraamine nucleus of cyclized polymer prepared from the same. For example, 2,3,5,6-tetraaminopyridine trihydrochloride is essentially insoluble in methanolic HCl, whereas 3,5-diamino-2,6-di(methylamino)pyridine trihydrochloride is readily soluble.

PREPARATION OF TETRAMINES

The tetramines of this invention are prepared from the corresponding 3,5- or 5,5'-dinitro analogs of compounds I and II, by hydrogenation. A preferred method of reduction consists in the use of a hydrogenation catalyst in the presence of a strong acid such as phosphoric, sulfuric, hydrochloric, hydrobromic, lower alkanesulfonic acids, perfluoroalkanesulfonic acids, and perfluoroacetic acid, and using a lower alcohol, polyfluorinated alcohol, or alkoxyalcohol, acetic acid, or propionic acid as cosolvent. Where a very strong acid such as trifluoromethanesulfonic acid is used, low concentrations, often equivalent to or less than the number of final amine groups may be employed. Isolation and recovery of the acid salt of the tetramino compound is readily effected by separation from the catalyst with subsequent removal of volatiles or precipitation with non-solvent. Tetramine acid salts can be used for preparing other salts or mixed acid salts. The hydrobromide, trifluoroacetate and alkanesulfonate salts are desirable for polymerization reactions because of their greater solubility as compared to the corresponding hydrochloride salts.

The 3,5-dinitro precursors of compound I can be prepared by the following methods:

a. nitration of a 2,6-di($R_1NH$)-4($R_2$)-pyridine in which each of $R_1$ and $R_2$ represents H, methyl, ethyl, propyl, butyl or pentyl and $R_1$ and $R_2$ are not required to be the same;

b. reaction of a 2,6-di($R_4NH$)-4-($R_2$)-3,5-dinitropyridine with at least one primary amine represented by the formula $R'NH_2$ wherein each R' is selected from lower alkyl or alkenyl, aminoalkyl, (N,N-dialkylamino)alkyl, cyanophenylalkyl, arylalkyl, (aminoaryl)alkyl, with subsequent reaction of the amino group of aminoalkyl and (aminoaryl)alkyl, and

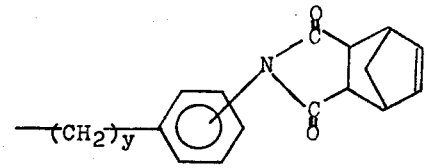

in which y = 1 or 2; and wherein $R_2$ is either H, methyl, ethyl, propyl, butyl or pentyl and $R_4$ is either H,

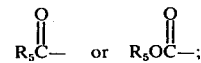

$R_5$ being either methyl, ethyl, propyl or butyl;

c. reaction of a 2,6-di($R_6NH$)-4-($R_2$)-3,5-dinitropyridine with at least one primary amine represented by the formula $R''NH_2$; wherein $R_6$ is either

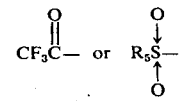

(in which $R_5$ is either methyl, ethyl, propyl or butyl) and $R_2$ is either H, methyl, ethyl, propyl, butyl or pentyl and each R'' is any of phenyl; alkylated or halo phenyl; pyridyl and alkylated pyridyl; quinolyl; amino phenyl or amino pyridyl with subsequent reaction of the amino group; $-C_6H_4SO_3\theta$; $-C_6H_4COO\theta$; $-ArCN$; $-Ar-Ar$;

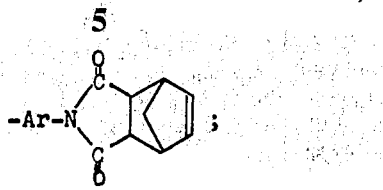

and —ArSR$_7$ in which R$_7$ is H, lower alkyl or phenyl and Ar represents phenyl or phenylene with up to one ring CH being replaced by N; and d. reaction of a 2,6-dihalo-4-(R$_3$)-3,5-dinitropyridine with a primary aliphatic or aromatic amine in the same manner as for the reaction of 2-halo-3,5-dinitropyridine with amines as described in Bull. Acad. Polon. Sci., Ser. Sci. Chim. 8 (5), 219 (1960) and Roczniki Chem. 43 (11), 1961 (1969) where halo may be any of F, Cl or Br.

Method (a) above has been previously described for the nitration of 2,6-diaminopyridine in my U.S. Pat. No. 3,740,410. This method is unsuitable for the preparation of 3,5-dinitro precursors to compound I where R$_1$ is alkenyl or phenyl or other substituents which will oxidize or nitrate under the reaction conditions necessary to produce the 3,5-dinitropyridine derivative.

Method (b) is preferably carried out with an excess primary aliphatic or arylalkyl amine, at temperatures between room temperature and 190°C in primary amine as solvent or in a polar aprotic solvent such as dimethylsulfoxide, N,N-dimethylformamide, N,N-dimethylacetamide, N-methylpyrrolidinone, tetramethylenesulfone, hexamethylphosphoramide, or mixtures thereof, or mixtures with less polar, unreactive aprotic solvents. The temperature of reaction is governed by the basicity and geometry of the primary amine. In general, less basic amines or sterically hindered amines require higher temperatures. For example, methylamine (pk$_b$=10.7) can be reacted with diethyl 3,5-dinitro-2,6-pyridinedicarbamate at room temperature to about 50°C in a mixture of dimethylsulfoxide and N,N-dimethylformamide, giving excellent yields of 2,6-di(methylamino)-3,5-dinitropyridine. Higher temperatures are required to achieve these yields using allylamine (pk$_b$=9.5) and even higher temperatures are required with the more hindered benzylamine (pk$_b$=9.4). Aromatic or heterocyclic primary amines of low basicity (pk$_b$ of about 7 or less) are unsatisfactory in this reaction.

Representative primary amines suitable for method (b) include methylamine, n-butylamine, allylamine, crotylamine, 1,2-diaminoethane (large excess), benzylamine, β-phenethylamine, β-(p-cyanophenyl)ethylamine, 3-(dimethylamino)propylamine, p-aminobenzylamine.

Method (c) is carried out in the same manner as method (b), but at some temperatures not lower than 70°C. Representative primary amines suitable for method (c) include aniline, p-toluidine, m-phenylenediamine (large excess), 2,6-diaminopyridine (large excess), the mono-aminopyridines, 4-aminobiphenyl, 4-(4'-aminophenyl)pyridine, 2-aminoquinoline, the monoimide 1:1 adduct of m-phenylenediamine and endo-cis-bicyclo[2.2.1]-5-heptene-2,3-dicarboxylic anhydride, the alkali or quaternary ammonium salts of p-aminobenzoic or sulfanilic acids, p-aminothiophenol, and 4-aminostilbene. 3,5-dinitro precursors to compound I where R$_1$ has labile reactive groups such as —CN, —CO$_2$C$_6$H$_5$, and

generally cannot be prepared directly from commercially available amines. Compounds containing the imide group

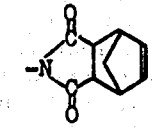

may be prepared via method (b) using the amine

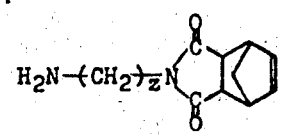

or via method (c) using the amine

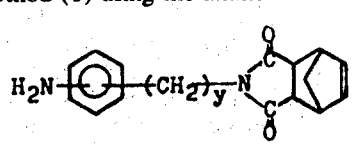

where up to one aromatic CH may be replaced by nitrogen and y is 0, 1 or 2 and z is 2, 3, or 4. Alternately the imide containing compounds may be prepared by reaction of 2,6-di(R$_4$NH)-4-(R$_2$)-3,5-dinitropyridine or 2,6-di(R$_5$NH)-4-(R$_2$)-3,5-dinitropyridine with a large excess of diamine H$_2$N(CH$_2$)$_z$NH$_2$ or

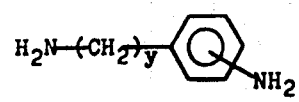

with subsequent reaction with

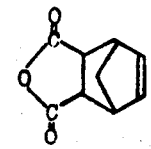

(endo-cis-bicyclo[2.2.1]-5-heptene-2,3-dicarboxylic anhydride). Finally compounds containing -CN or

bonded directly to a ring position of an aromatic amine are not particularly reactive in the process of method (c) but may be prepared by use of an aromatic amine substituted with a carboxylate group, followed by conversion of the carboxylate group to —CN or

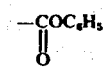

by well known methods.

The 3,5-dinitropyridine compounds used in methods (b) and (c) above are prepared by nitration of the corresponding 2,6-diaminopyridines or N,N'-substituted derivatives thereof as described in my U.S. Pat. No. 3,740,410 or in U.S. Pat. application Ser. No. 151,601 filed June 9, 1971. The N,N'-substituted 2,6-diaminopyridines such as the acetamido, carbamate, or sulfonamido derivatives are each prepared by known methods.

The dinitro intermediates to compounds of Formula II are prepared by nitration of the corresponding 4,4'-di($R_3$NH)- or 6,6'-di($R_3$NH)-bipyridyl compounds by methods taught in the art, such as the nitration of 4,4'-diamino-2,2'-bipyridine described in British Specification 1,115,607. The di(alkylamino) bipyridyl compounds are in turn prepared by amination at elevated temperatures of the corresponding 4,4'-dihalo- or 6,6'-dihalo-bipyridines.

The principal utility of the tetramines of this invention resides in utilizing their acid salts for the production of thermally stable polymers by processes described in my U.S. Pat. Application Ser. No. 151,601 and in the present application.

This process essentially involves reacting a suitable tetramine acid salt with an essentially equimolar amount of bis(acid halide), the halide being selected from —Cl, -Br and -F, in a polar aprotic solvent at temperatures ranging from about −10°C to about 70°C and preferably below 40°C to afford soluble high molecular weight precyclized intermediates (III and IV) to substituted polybenzimidazoles (V and VI). The precyclized polymers can be chemically or thermally cyclodehydrated to the substituted polybenzimidazoles.

—CH=CH—, 5- and 6- membered heteroaromatics containing at least one nitrogen atom and mixtures thereof, and substituted aromatic radicals where the substituents are selected from lower alkyl, F, Cl, —CN, —$SO_3$H, and

the inorganic/organic radicals consisting of ferrocenyl, carboranyl, and biaryls separated by at least one phosphorus atom or by at least one silanyl or siloxanyl group, and mixtures thereof; $R_7$ represents H, lower alkyl or phenyl; $R_1$, $R_2$, $R_3$ and X are as defined in compounds I and II; and the symbol → indicates possible isomerism. An acid salt of more than one tetraamino compound and more than one bis(acid halide) compound may be reacted to form the precyclized products providing that the total moles

Precyclized

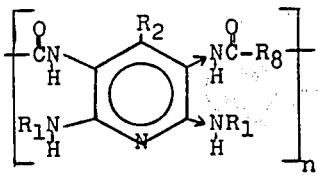

Formula III

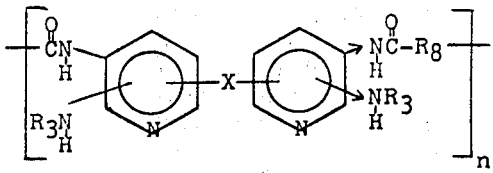

Formula IV

Cyclodehydrated

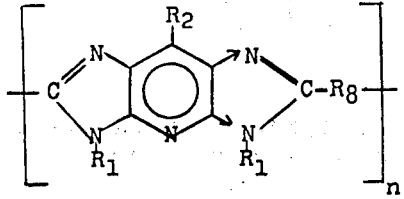

Formula V

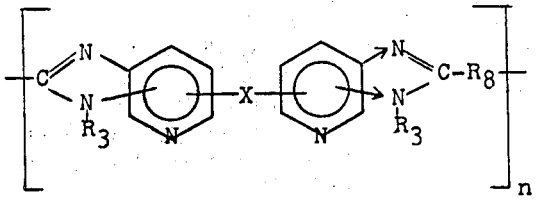

Formula VI in which $R_8$ is a divalent paraffinic, perfluoroalkyl, perfluoropolyalkylene oxide, alkenyl, aromatic or inorganic/organic radical including acylic paraffinic, cycloparaffinic, carbocyclic radicals and heterocyclic radicals having a single, multiple or fused ring structure, the multiple ring structures including polyarylenes with 2 to 9 aryl rings in which the aryl groups are bonded directly to each other or bridged by a divalent member selected from the group consisting of alkylene with up to 3 carbon atoms,

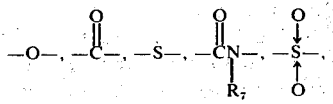

of acid salts is essentially equal to the total moles of bis(acid halides).

Bis(acid halides) which contain a carbalkoxy group ortho or peri to one or both acid halide groups which $R_8$ is arylene or heteroarylene or located 1,2 or 1,3 when $R_8$ is alkylene or cycloalkylene afford precyclized polyamide precursors upon reaction with the tetraamines I and II, preferably when $R_1$ and $R_3$ of I and II, respectively are hydrogen. However, the cyclodehydrated products of these precyclized polymers (for $R_1$ and $R_3$ = H) are not polybenzimidazoles represented by V and VI, but are the related poly(benzimidazole/imidazopyrrolones) and polyimidazopyrrolones ("pyrrones"), represented by Formulae VII and VIII, respectively:

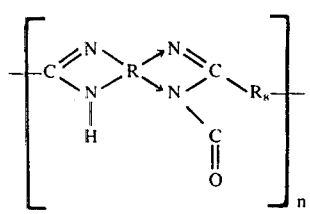
Formula VII
($R_8$ is trivalent here)

and

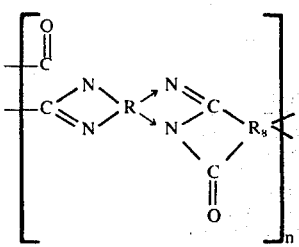
Formula VIII
($R_8$ is tetravalent here)

where R is a tetravalent heteroaromatic radical represented by:

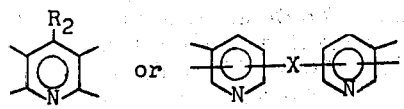

and the symbol represents possible isomerism.

Polymers represented by VII and VIII where R is

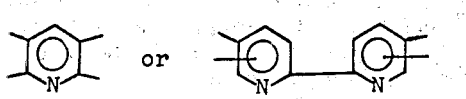

and $R_8$ is selected from the group alkylene, cycloparaffinic, monocyclic aryl or heteroaryl, diaryl, diaryls bridged by alkylene of 1 to 3 carbon atoms,

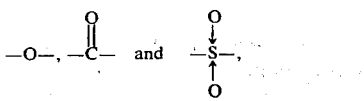

and fused carbocyclic and heteroarylene structures containing 2 and 3 rings are described in U.S. Pat. Application Ser. No. 151,601. It has been found that polymers VII and VIII where $R_8$ is selected from polyarylene radicals containing 3 to 9 aryl groups bonded linearly or organic/inorganic radicals containing one or more of the elements B, Fe, or Si show improved solubility and processability as compared with the polymers derived from mono(acid halide) anhydrides and dianhydrides described in said United States Patent Application.

Polymers VII and VIII can also be obtained by reaction of tetraamines I (where $R_1$=H) and II (where $R_3$=H) with mono(acid halide) anhydrides of tribasic acids and dianhydrides of tetrabasic acids, respectively, to give the precyclized polyamide precursors IX and X which upon cyclodehydration afford VII and VIII, respectively.

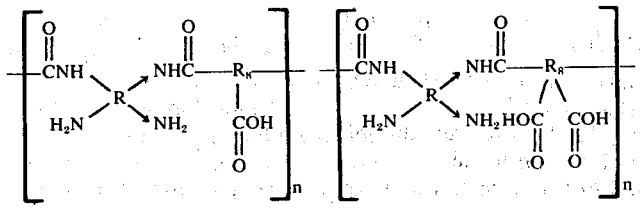

Formula IX          Formula X

Each -COOH group of $R_8$ in IX and X is located 1,2 or 1,3 to the $$-\overset{\text{O}}{\underset{\|}{C}}NH-$$

group on carbons of the $R_8$ group when $R_8$ is alkylene or cycloalkylene, and ortho or peri to the $$-\overset{\text{O}}{\underset{\|}{C}}NH-$$

group when $R_8$ is aromatic or heteroaromatic.

EXAMPLE 1

Preparation of 2,6-diamino-4alkyl-3,5-dinitropyridines

To a solution (0°C) of 2,6-diamino-4-methylpyridine (123 g, 1.0 mole) in 500 ml conc. $H_2SO_4$ was gradually added, with good stirring, 90% $HNO_3$ (2.5 moles). The nitration mixture was kept at 0°–10°C for 2 hours. 2,6-Diamino-4-methyl-3,5-dinitropyridine was isolated in 65% yield by pouring the nitration mixture onto ice, filtering product and washing well with methanol and then water. Anal. Calcd for $C_6H_7N_5O_4$: C, 33.8; H, 3.3; N, 32.9. Found: C, 33.6; H, 3.4; N, 32.9.

In a similar manner by replacing the 2,6-diamino-4-methylpyridine by 2,6-diamino-4-ethylpyridine or by 2,6-diamino-4-n-propylpyridine, a good yield of the corresponding 2,6-diamino-4-alkyl-3,5-dinitropyridine was obtained.

EXAMPLES 2–5

Following a procedure similar to that of Example 1, but substituting the diamine derivative indicated below for 2,6-diamino-4-methylpyridine the corresponding 3,5-dinitro compounds of Examples 2–5 were obtained.

| Example | Diamine Derivative | Reaction Conditions °C | Hrs. | Dinitro Product |
|---|---|---|---|---|
| 2 | Diethyl 4-methyl-2,6-pyridine dicarbamate | 5–10<br>20–30 | 1<br>2 | diethyl 4-methyl-3,5-dinitro-2,6-pyridine dicarbamate |
| 3 | 4-methyl-2,6-pyridine-dimethane-sulfonamide | 20–30<br>50–60 | 2<br>2 | 4-methyl-3,5-dinitro-2,6-pyridine dimethane-sulfonamide |
| 4 | 2,6-diacetamido-4-ethylpyridine | 0–5<br>20–30 | 2<br>1 | 2,6-diacetamido-4-ethyl-3,5-dinitro-pyridine |
| 5 | 2,6-di(trifluoro-acetamido)-4-n-pentyl-pyridine | 20–30<br>50–60 | 2<br>2 | 2,6-di(trifluoro-acetamido)-4-n-pentyl-3,5-dinitropyridine |

EXAMPLE 6

Preparation 4,4'-di(methylamino)-5,5'-dinitro-2,2'-dipyridyl

To a stirred, cooled (−5° to 0°C) solution of 4,4'-di(-methylamino)-2,2'-dipyridyl (107 g, 0.5 mole) in 400 ml conc. $H_2SO_4$ was gradually added a solution of 45 ml of 90% $HNO_3$ in 50 ml conc. $H_2SO_4$. The reaction was allowed to warm up to room temperature and after 2 hours, was gradually heated to 90°C. The temperature was maintained at 90°–100°C for 1.5 hours, cooled and poured onto crushed ice. Acids were neutralized below 15°C to a pH of about 4 by addition of conc. aqueous $NH_3$. The yellow precipitate that formed was filtered off, washed well with water and vacuum dried to give 4,4'-di(methylamino)-5,5'-dinitro-2,2'-dipyridyl (61%). Anal. Calcd. for $C_{12}H_{12}N_6O_4$: C, 47.4; H, 4.7 N, 27.6. Found: C, 47.5; H, 4.8; N, 27.4.

EXAMPLES 7–12

Following a procedure similar to that described in Example 6, but substituting the amino heterocycle indicated below for 4,4'-di(methylamino)-2,2'-bipyridine and using a final temperature of 50°–60°C for Examples 9 and 10, the corresponding 5,5'-dinitro compounds of Examples 7–11 and the corresponding 5',5''-dinitro compound of Example 12 were obtained.

| Example | di(alkylamino)compound to be nitrated |
|---|---|
| 7 | 4,4'-di(n-butylamino)-2,2'-bipyridine |
| 8 | 6,6'-di(methylamino)-2,2'-bipyridine |
| 9 | 1,3-bis(6-amino-2-pyridyl) propane |
| 10 | di(6-amino-2-pyridyl)ether |
| 11 | 6,6'-di(n-propylamino)-3,3'-bipyridine |
| 12 | 6',6''-diamino-2:6-di-2'-pyridylpyridine |

EXAMPLE 13

Preparation of 2,6-di(methylamino)-3,5-dinitropyridine

To a solution of 2,6-diamino-3,5-dinitropyridine (25.0 g, 0.125 mole) and 225 ml dimethylsulfoxide in a 500 ml Parr bottle was added a solution of methylamine (20 g, 0.65 mole) in 75 ml N,N-dimethylacetamide (DMAc). The reaction was shaken for 4 hours at ambient temperatures and then heated 20 hours at 70°C. Upon cooling, the heterogeneous mixture was diluted with 100 ml methanol, filtered, washed with 200 ml DMAc-methanol (lv/lv), twice with methanol and dried. 2,6-Di(methylamino)-3,5-dinitropyridine, m.p. 323°–325°C (dec.) was obtained as a golden yellow solid (25.0 g, 93% yield). This product, unlike 2,6-diamino-3,5-dinitropyridine, is essentially insoluble in dimethylsulfoxide and 85% $H_3PO_4$. Anal. Calcd. for $C_7H_9N_5O_4$: C, 37.0; H, 4.0; N, 30.8. Found: C, 37.2; H, 3.8; N, 31.0.

EXAMPLES 14–23

Following a procedure similar to that described for Example 13, but substituting the 2,6-diamino-3,5-dinitropyridine and methylamine by the dinitro compound represented by the formula

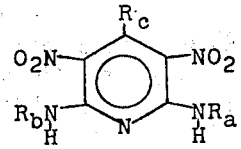

and amine ($RNH_2$) indicated below, the following 3,5-dinitropyridine derivatives of Examples 14–23 were obtained where the $R_a$ and $R_b$ groups of starting material are replaced by the R group of the amine.

| Ex. | Dinitro Starting Material $R_a=$ | $R_b=$ | $R_c=$ | Amine Co-reactant $RNH_2$, R= | Reaction Conditions °C | Hrs. |
|---|---|---|---|---|---|---|
| 14 | H | H | $CH_3$— | $CH_3$— | 70 | 20 |
| 15 | $CH_3\overset{O}{\overset{\|}{C}}$— | $CH_3\overset{O}{\overset{\|}{C}}$— | $C_2H_5$— | n-$C_4H_9$— | 70 | 20 |
| 16 | H | H | H | $CH_2$=CH—$CH_2$— | 70<br>90–100 | 20<br>10 |
| 17 | $C_2H_5O\overset{O}{\overset{\|}{C}}$— | $C_2H_5O\overset{O}{\overset{\|}{C}}$— | $CH_3$— | $CH_3CH$=CH—CH-$_2$—* | 70<br>90–100 | 20<br>10 |

| Ex. | Dinitro Starting Material $R_a=$ | $R_b=$ | $R_c=$ | Amine Co-reactant $RNH_2$, R= | Reaction Conditions °C | Hrs. |
|---|---|---|---|---|---|---|
| 18** | H | H | H | $C_2H_5-$(50 mole %); $n-C_4H_9-$(50 mole %) | 70 | 24 |
| 19 | $CH_3\overset{O}{\underset{\|}{C}}-$ | $CH_3\overset{O}{\underset{\|}{C}}-$ | H | $C_6H_5CH_2-$* | 70<br>90–100 | 20<br>20 |
| 20 | H | H | H | $(CH_3)_2NC_5H_4-$ | 25<br>50 | 5<br>20 |
| 21 | H | H | H | $p-CN-C_6H_4-$<br>$CH_2CH_2-$ | 50<br>80–90 | 10<br>24 |
| 22 | H | H | H | $H_2NCH_2CH_2-$<br>(500% excess) | 25<br>50–60 | 5<br>10 |
| 23 | $CH_3\overset{O}{\underset{\|}{C}}-$ | $CH_3\overset{O}{\underset{\|}{C}}-$ | $CH_3-$ | $2-C_5H_4NCH_2-$*<br>(2-pyridyl) | 70<br>90 | 10<br>20 |

*1.0 mole $RNH_2$ employed
**Product after fractionation and purification was 2-ethylamino-6-n-butylamino-3,5-dinitropyridine.

EXAMPLE 24

Preparation of 2,6-dianilino-3,5-dinitropyridine

Under a nitrogen atmosphere, a mixture of 3,5-dinitro-2,6-pyridine dimethanesulfonamide (50 g, 0.14 mole), 200 ml aniline and 250 ml N,N-dimethylacetamide was heated with stirring to 140°C and then maintained at this temperature for 6 hours. The warm (90°C) mixture was poured onto 450 ml methanol with stirring and 20 ml triethylamine added. The precipitate was washed with methanol and dried to afford 2,6-dianilino-3,5-dinitropyridine (34.5 g, 70%) as an orange solid, mp. 224–225.5. Anal. Calcd. for $C_{17}H_{13}N_5O_4$: C, 58.1; H, 3.7. Found: c, 57.4; H, 3.4.

The above product was also obtained by using aniline as sole reactant-solvent at 130°–150°C for 24 hours.

EXAMPLES 25–34

Following a procedure similar to that described in Example 24 using reaction temperatures of 120°–180°C and reaction times of 2–24 hours and substituting the 2,6-dimethanesulfonamido-3,5-dinitropyridine and aniline by the 3,5-dinitropyridine indicated by the formula

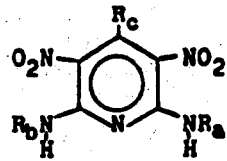

and the amine $RNH_2$, respectively the 3,5-dinitropyridine derivatives of Examples 25–34 were obtained where the $R_b$ and $R_a$ groups of starting material were replaced by the R group of the amine co-reactant.

| Ex. | Dinitro Starting Material $R_a=$ | $R_b=$ | $R_c=$ | Amine Co-reactant $RNH_2$, R= |
|---|---|---|---|---|
| 25 | $C_2H_5SO_2-$ | $C_2H_5SO_2-$ | $CH_3-$ | $p-C_2H_5C_6H_4-$ |
| 26 | $CF_3\overset{O}{\underset{\|}{C}}-$ | $CF_3\overset{O}{\underset{\|}{C}}-$ | H | $2-H_2NC_5H_4N-$(2-aminopyridyl) |
| 27* | $CH_3SO_2-$ | $CH_3SO_2-$ | H | $(CH_3)_4N^+{}^-O-\overset{O}{\underset{O}{\overset{\|}{S}}}-C_6H_4-(p)$ |
| 28* | $CH_3SO_2-$ | $CH_3SO_2-$ | H | $K^+{}^-O\overset{O}{\underset{\|}{C}}-C_6H_4-(m)$ |
| 29 | $CH_3SO_2-$ | $CH_3SO_2-$ | $CH_3-$ | 2-quinolyl |
| 30 | $CH_3SO_2-$ | $CH_3SO_2-$ | $CH_3-$ | $p-C_6H_5-C_6H_4-$ |
| 31 | $CH_3SO_2-$ | $CH_3SO_2-$ | H | $p-HS-C_6H_4-$ |
| 32 | $CH_3SO_2-$ | $CH_3SO_2-$ | H | $m-H_2NC_6H_4-$ (500% mole excess) |
| 33 | $CH_3SO_2-$ | $CH_3SO_2-$ | H | $p-C_6H_5CH=CHC_6H_4-$ |
| 34 | $CH_3SO_2-$ | $CH_3SO_2-$ | $C_2H_5-$ | $m-ClC_6H_4-$ |

*Acidification of product with excess HCl resulted in formation of the acid form, i.e. $-SO_3H$ or $-CO_2H$.

EXAMPLE 35

Preparation of 2-anilino-3,5-dinitro-6-methanesulfonamidopyridine and hydrolysis to 2-amino-6-anilino-3,5-dinitropyridine A flask was charged with 3,5-dinitro-2,6-pyridine-dimethanesulfonamide (5.3 g, 0.015 mole), acetic acid (7.5 g) and aniline (20 g, 0.215 mole). An immediate deep red precipitate formed. The mixture was heated under nitrogen for 14 hours at 87°C and for 3½ hours at 120°C and cooled. The homogeneous mixture was diluted with methanol-water to precipitate product which was washed with methanol and vacuum dried. A golden yellowlight orange solid (4.2 g) m.p. 210°–215°C was obtained. Recrystallization from acetone, followed by a methanol wash, and drying raised the m.p. to 214°–218°C. Anal. Calcd. for $C_{12}H_{11}N_5O_6S$: C, 40.8; H, 3.1; N, 19.9; S, 9.1. Found: C, 42.1; H, 3.1; N, 19.4; S. 8.7. This product, unlike the product of Example 24, is soluble in methanol containing triethylamine.

The above product (5 g) was dissolved in warm 70% $H_2SO_4$ (40 g) and heated at 140°C. The mixture was cooled, poured onto ice water to precipitate 2-amino-6-anilino-3,5-dinitropyridine.

EXAMPLE 36

Preparation of 2-(α-pyridylamino)-3,5-dinitro-6-methanesulfonamidopyridine

A flask was charged with 3,5-dinitro-2,6-pyridinedimethonesulfonamide (7.0 g, 0.0197 mole), acetic acid (10g), and 2-aminopyridine (20 g, 0.213 mole) which was heated under nitrogen for 5¼ hours at 110°C. The mixture was cooled, diluted with methanol to precipitate product which was filtered, washed, and dried. The 2-(α-pyridylamino)-3,5-dinitro-6-methanesulfonamidopyridine (6.3 g) so obtained had a m.p. of 165°–170°C. Anal. Calcd. for $C_{12}H_{10}N_6O_6S$: C, 37.3; H, 3.0; N, 23.7. Found: C, 35.5; H, 3.6; N, 23.1.

EXAMPLE 37

Preparation of 3,5-diamino-2,6-di(methylamino)pyridine acid salts

A. Trismethanesulfonate Salt

A 250 ml Parr bottle was charged with 2,6-di(methylamino)-3,5-dinitropyridine (20.0 g, 0.088 mole), 30 ml methanesulfonic acid, 200 ml methanol and 1.0 g 5% Pd/charcoal catalyst. The mixture was subjected to hydrogenation at ambient temperature with an initial hydrogen pressure of 65 psig. When no further uptake of hydrogen was observed, the mixture was treated with anhydrous silica gel (25 g), filtered free of catalyst and drying agent under a nitrogen atmosphere, and methanol removed under vacuum. The trimethanesulfonate salt of 3,5-diamino-2,6-di(methylamino)pyridine was obtained under nitrogen by addition of cold i-butanol-benzene to the concentrate, followed by vacuum drying (40°–50°C) over $P_2O_5$.

B. Tris(trifluoroacetate) Salt

The procedure of example 37A was followed except that $CF_3CO_2H$ (50 ml) and acetic acid (200 ml) was substituted for the methanesulfonic acid and methanol, respectively. The tris(trifluoroacetate) salt was obtained directly after complete removal of acetic acid under high vacuum.

C. Trihydrohalide Salts

The procedure of Example 37B was repeated except that when approximately three quarters of the solvent was removed, the concentrate was added under nitrogen to 125 ml 10% HCl in isopropyl alcohol (0°C). The precipitate was filtered under nitrogen, washed with additional cold 10% HCl in isopropyl alcohol, and vacuum dried over $P_2O_5$ to afford 3,5-diamino-2,6-di(methylamino)pyridine trihydrochloride.

Trishydrochloride, in contrast to 2,3,5,6-tetraaminopyridine trihydrochloride, was considerably soluble in concentrated HCl or in methanolic hydrogen chloride.

D. Sulfuric Acid Salt

The procedure of Example 37A was repeated except that 30 ml conc. $H_2SO_4$ was substituted for the methanesulfonic acid. The tris(sulfuric acid) salt was obtained by addition of the filtered hydrogenation concentrate to cold (0°C) isopropyl alcohol followed by washing and vacuum drying.

EXAMPLE 38

Preparation of 2,3,5,6-tetraamino-4-methylpyridine acid salts

A. Trihydrochloride Salt

A 500 ml Parr bottle was charged with 2,6-diamino-4-methyl-3,5-dinitropyridine (21.3 g, 0.10 mole), 150 ml 85% $H_3PO_4$, 150 ml methanol and 5% Pd/charcoal catalyst (3.0 g). The mixture was placed under 65 psig hydrogen pressure and then heated gradually to about 45°C and maintained at this temperature until no further hydrogen uptake was observed. The cooled mixture was filtered under nitrogen, the cold filtrate was diluted with 250 ml cold conc. HCl and then saturated with HCl at 0°C. The precipitate was filtered under nitrogen, washed with 10% HCl in isopropyl alcohol and vacuum dried at 70°–80°C over $P_2O_5$ to afford 2,3,5,6-tetraamino-4-methylpyridine trihydrochloride (16.3 g, 62%). Anal. Calcd. for $C_6H_{11}N_5 \cdot 3HCl$: C, 27.5; H, 5.3; N, 26.7; Cl, 40.6. Found: C, 27.3; H, 5.5; N, 26.5; Cl, 40.5.

B. Trismethanesulfonate Salt

The hydrochloride salt (10 g) of Example 38A was dissolved in methanesulfonic acid (60 g) and the resulting solution evacuated to remove HCl. Precipitation into cold isopropyl alcohol afforded the trismethanesulfonate salt.

EXAMPLE 39

Preparation of 3,5-diamino-2,6-dianilinopyridine dihydrochloride

A 500 ml Parr bottle was twice charged with 2,6-dianilino-3,5-dinitropyridine (13.5 g, 0.0385 mole), 300 ml of methanol containing HCl (10 g) and 5% Pd/Charcoal catalyst (1.1 g). The mixture was placed under 55 psig. hydrogen pressure and kept at 25°–40°C until no further uptake of hydrogen was observed. The combined reduction mixtures were cooled, precipitated product and catalyst filtered under nitrogen, and the filter cake washed with 10% HCl in isopropyl alcohol. The filter cake was added to 500 ml of warm (55°C) conc. HCl, stirred well for 5 minutes, filtered and the insolubles washed with conc. HCl. The clear filtrate was cooled (0°C), diluted with 500 ml cold (−15°C) isopropyl alcohol with good stirring to precipitate product. The solid was filtered, washed with 10% HCl in isopropyl alcohol and vacuum dried over $P_2O_5$ to afford 3,5-diamino-2,6-dianilinopyridine dihydrochloride (25.5 g, 92%). Anal. Calcd. for $C_{17}H_{17}N_5.2HCl$: C, 56.0; H, 5.2; N, 19.2; Cl, 19.5. Found: C, 54.0; H, 5.4; N, 19.4; Cl, 20.0.

EXAMPLE 40

Preparation of 5,5',6,6'-tetraamino-2,2'-dipyridyl and acid salts thereof

The reduction procedure employed was similar to that described in British Specification No. 1,115,607 for the preparation of 4,4',5,5'-tetraamino-2,2'-dipyridyl from 4,4'-diamino-5,5'-dinitro-2,2'-dipyridyl. A 500 ml Parr bottle was charged with 13.8 g (0.05 mole) 6,6'-diamino-5,5'-dinitro-2,2'-dipyridyl, 250 ml acetic acid and 1.0 g 5% Pd/Charcoal catalyst. The mixture was subjected to hydrogenation at about 60°C. When no further uptake of hydrogen was observed, the mixture was cooled, filtered free of catalyst, and treated with 9.1 g (0.25 mole) of anhydrous HCl (use of HBr will afford the tetrahydrobromide salt). The mixture was cooled to 0°C with good stirring, product filtered off, solid washed with tetrahydrofuran and dried to afford 5,5'-6,6'-tetraamino-2,2'-dipyridyl tetrahydrochloride. Anal. Calcd. for $C_{10}H_{12}N_6.4HCl$: Cl, 39.2. Found: Cl, 39.0.

The bis(trifluoromethanesulfonate) salt was likewise obtained by conducting the reduction in the presence of 0.10 mole $CF_3SO_3H$. This salt was isolated by filtering off catalyst, vacuum stripping of solvent, precipitation with cold tetrahydrofuran, filtering and vacuum drying.

The free base 5,5',6,6'-tetraamino-2,2'-dipyridyl could be obtained by dissolving either of the above amine salts in water, heating with decolorizing charcoal, filtering, cooling the filtrate to about 0°C under a nitrogen purge and adding concentrated aqueous ammonia to neutralize all the acid. The solid tetraamine was obtained by filtration and drying.

EXAMPLES 41–53

The polyamino acid salts of Examples 41–53 were prepared by using the dinitro intermediates indicated below and following the reduction procedures of Example 37, 38, 39 or 40.

| Ex. | Dinitro Starting Material | Polyamine* Isolated as Polysalt of |
|---|---|---|
| 41** | 2,6-di(allyamino)-3,5-dinitropyridine | $CF_3CO_2H$ |
| 42 | 2-amino-6-anilino-3,5-dinitropyridine | HCl |
| 43 | 2,6-diamino-4-ethyl-3,5-dinitropyridine | $CH_3SO_3H$ |
| 44 | 2,6-di-(α-pyridylamino)-3,5-dinitropyridine | $CH_3SO_3H$ |
| 45 | 2,6-di(benzylamino)-3,5-dinitropyridine | HCl |
| 46 | 2,6-di(n-butylamino)-4-ethyl-3,5-dinitropyridine | $H_2SO_4$ |
| 47 | 2,6-di(m-cyanoanilino)-3,5-dinitropyridine | HCl |
| 48 | 2,6-di(p-sulfoanilino)-3,5-dinitropyridine | $CH_3SO_3H$ |
| 49 | 6,6'-di(methylamino)-5,5'-dinitro-2,2'-bipyridine | HCl |
| 50 | di(5,6-diamino-2-pyridyl) ether | HCl |
| 51 | 6',6''-diamino-5',5''-dinitro-2:6-di-2'-pyridylpyridine | HBr |
| 52 | 2,6-di($R_1$)-3,5-dinitropyridine where $R_1=$ 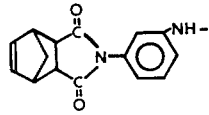 | $H_2SO_4$ |
| 53 | 2,6-di(benzylamino)-3,5-dinitropyridine | HCl |

*Each nitro group of starting material is replaced by a $-NH_2$ group.
**The procedure of Example 37B was followed except that the $CF_3CO_2H$ (3.3 equiv/mole of dinitro intermediate) was added after filtration of catalyst.

EXAMPLE 54

Precyclized Polymer and Polybenzimidazole from 3,5-Diamino-2,6-di(anilino)pyridine Dihydrochloride and Isophthaloyl Chloride Isophthaloyl chloride (5.16 g, 0.0254 mole) was added over 5 minutes under a nitrogen atmosphere to a stirred cold mixture of 9.25 g (0.0254 mole) 3,5-diamino-2,6-di(anilino)pyridine dihydrochloride and 45 g N-methylpyrrolidinone. The reaction was maintained at 5°–10°C for several hours and then kept at room temperature for 21 hours. The polymer solution was poured into 200 ml methanol with good stirring. The precipitate of precyclized polymer was filtered, washed well with methanol twice and vacuum dried overnight at 50°–55°C. The polymer (9.8 g) was obtained as a yellow-green powder which was soluble in N,N-dimethylformamide (DMF), dimethylsulfoxide (DMSO), and formic acid. Anal. Calcd. for $C_{25}H_{19}N_5O_2.HCl$: C, 65.5; H, 4.4; N, 15.3; Cl, 7.8. Found: C, 67.5; H, 4.6; N, 15.4; Cl, 2.9.

This polymer was isolated as its neutral salt as follows: the hydrochloride polymer (3.0 g) was dissolved in DMF (25 ml), treated with triethylamine (0.7 g) and then precipitated into methanol and purified as described above. The neutral precyclized polymer was soluble in DMF, DMSO and formic acid. Anal. Calcd. for $C_{25}H_{17}N_5O_2$: C, 71.3; H, 4.5; N, 16.6. Found: C, 71.1; H, 4.7; N, 16.6.

Similarly other acid salts of the above precyclized polymer may be formed by replacing the dihydrochloride salt by one of the following 3,5-diamino-2,6-di(anilino)pyridine bis(acid salts); hydrobromide, methanesulfonate, or trifluoroacetate.

The above precyclized hydrochloride polymer (3.0 g) was converted to the cyclized polybenzimidazole (2.55 g) by heating two hours under vacuum at each of the following temperatures, 150°, 200°, 300°, and 350°C. The resulting polybenzimidazole was soluble in formic acid, $CF_3CO_2H$ and methanesulfonic acid. Anal. Calcd. for $C_{25}H_{15}N_5$: C, 77.9; H, 3.9; N, 18.2. Found: C, 77.8; H, 4.0; N, 18.1. This polymer possessed outstanding thermooxidative stability retaining 99% of its weight after 500 hours isothermal aging in air at 600°F (316°C). In comparison the polybenzimidazole derived from 2,3,5,6-tetraaminopyridine.3HCl and isophthaloyl chloride retained 87% of its weight after 300 hours and poly[2,2'-(m-phenylene)-5,5'-bibenzimidazole] retained only 57% of its weight after 200 hours in air at 600°F.

EXAMPLE 55

Precyclized Polymer and Polybenzimidazole from 3,5-Diamino-2,6-di(anilino)pyridine Dihydrochloride and 4,4'-[sulfonyl-bis(p-phenyleneoxy)]di-benzoyl Chloride The polymerization described in Example 1 was repeated using 10.36 g (0.0196 mole) 4,4'-[sulfonyl-bis(p-phenyleneoxy]-dibenzoyl chloride and 7.15 g (0.196 mole) 3,5-diamino-2,6-(dianilino)pyridine dihydrochloride. The precyclized polymer which was obtained in excellent yield was very soluble in DMF, DMSo and formic acid. Anal. Calcd. for $C_{43}H_{31}N_5O_6S \cdot HCl$: C, 66.0; H, 4.1; N, 8.9; Cl, 4.5; S, 4.1. Found: C, 67.5; H, 4.3; N, 9.0; Cl, 1.1; S, 4.4. This polymer was redissolved in 75 ml DMF, and 5 ml triethylamine added. After stirring 15 minutes the polymer solution was precipitated into 400 ml methanol, filtered, washed and dried to give the neutral precyclized polymer (12.7 g, 87%). Anal. Calcd. for $C_{43}H_{31}N_5O_6S$: C, 69.3; H, 4.2; N, 9.4; S, 4.3. Found: C, 68.4; H, 4.6; N, 8.9; S, 4.4.

The above precyclized polymer (3.0 g) was converted to the cyclized polybenzimidazole (2.68 g) as described in Example 1. This polymer was insoluble in DMF or DMF-DMSO but was very soluble in formic acid or $CF_3CO_2H$ even when the latter solvent was diluted with hexafluoroisopropyl alcohol or 3,3,3,2,2-pentafluoropropanol. Anal. Calcd. for $C_{43}H_{27}N_5O_4S$: C, 72.8; H, 3.8; N, 9.9; S. 4.5. Found: C, 73.5; H, 3.9; N,9.2; S. 4.0.

The preceding description and Examples are intended to illustrate preferred embodiments of the invention and are not intended to limit the invention in any way. The monomers described are useful in the production of polymers in the same manner as the tetraamino pyridines utilized in my U.S. Pat. No. 3,740,410 issued June 19, 1973 and in U.S. Patents 3,783,137 issued Jan. 1, 1974 and 3,804,804 issued Apr. 16, 1974.

Accordingly, it is not intended that this invention be limited in any way except as defined in the claims which follow.

I claim:

1. 2,6-Di(substituted amino)-3,5-dinitropyridine compounds represented by a formula selected from the group consisting of

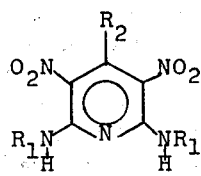

and

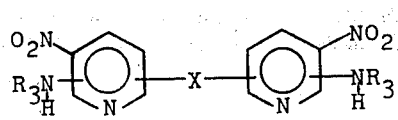

wherein $R_2$ represents a monovalent member selected from the group consisting of hydrogen, methyl, ethyl, propyl, butyl and pentyl;

$R_1$ represents a monovalent member selected from the group consisting of hydrogen, $C_1$-$C_5$ alkyl, substituted $C_1$-$C_5$ alkyl, $C_3$-$C_5$ alkenyl, phenyl, pyridyl, picolyl, quinolyl, substituted benzyl, and substituted phenyl wherein the substituents on said members are selected from the group consisting of methyl, phenyl, pyridyl, -CN, -COOH and its salts, -$SO_3$ and its salts, -$NH_2$,

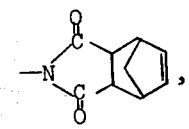

$COOC_6H_5$, -SH, thioaryl, thioalkyl, -CH=$CHC_6H_5$, and N,N-dimethylamino; with the proviso that not all three of the $R_1$ and $R_2$ members can be H; and both of the $R_1$'s need not be identical;

$R_3$ is a monovalent radical selected from the group consisting of H and alkyl of 1 to 5 carbon atoms; and x is a covalent bond or a divalent radical selected from the group consisting of alkylene of 1 to 3 carbon atoms, -S-, -O- and

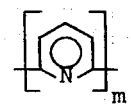

where m is equal to 1 or 2; and each $R_3NH$- group is located ortho to a nitro group and the pyridyl rings containing the amino groups are joined via the 2,2', 3,3', or 2,3' positions with the provisos that when X is a covalent bond both $R_3$'s cannot be hydrogen when the pyridyl groups are joined 2,2'; and when X is

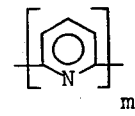

the pyridyl groups are joined 2,2'; and further that both of the $R_3$'s need not be identical.

2. A process for preparing the compounds of claim 1 which comprises reacting 1. a 2,6-di($R_4$NH)-4-$R_2$-3,5-dinitropyridine wherein $R_4$ represents a monovalent member selected from the group consisting of H-,

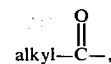

and

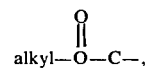

the alkyl in said group of alkyl with up to 5 carbon atoms, and $R_2$ is selected from the group consisting of H and alkyl with up to 5 carbon atoms, 2. at least one primary amine represented by the formula $R'NH_2$, wherein $R'$ is selected from the lower alkyl or alkenyl, aminoalkyl, (N,N-dialkylamino)alkyl, cyanophenylalkyl, arylalkyl, (aminoaryl)alkyl, and

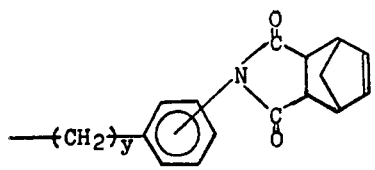

in which y = 1 or 2;

said reaction being effected at temperatures between about 25°C and 200°C in a solvent selected from the group consisting of primary amines and polar aprotic solvents and mixtures thereof.

3. A process for preparing 2,6-di(substituted amino)-3,5-dinitropyridine compounds which comprises: reacting a 2,6-di($R_6$NH)-4-$R_2$-3,5-dinitropyridine or a 2-($R_1$NH)-6-($R_6$NH)-4-$R_2$-3,5-dinitro-pyridine wherein $R_6$ represents

or

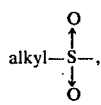

and $R_2$ is selected from the group consisting of H and alkyl with 1 to 5 carbon atoms, with at least one primary amine represented by the formula $R''NH_2$, and $R''$ is any of phenyl; alkylated or halo phenyl; pyridyl and alkylated pyridyl; quinolyl; amino phenyl or amino pyridyl; -$C_6H_4SO_3\theta$; —$C_6H_4COO\theta$; —ArCN; -Ar-Ar;

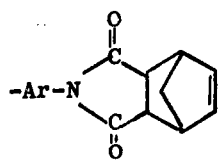

; and -Ar$SR_7$ in which $R_7$ is H, lower alkyl or phenyl; and Ar is phenyl or phenylene with up to one ring CH being replaced by N and effecting said reaction at a temperature between about 70°C and 200°C; $R_1$ is as defined in Claim 1.

4. Substituted tetraamino pyridine compounds represented by one of the formulae from the group consisting of

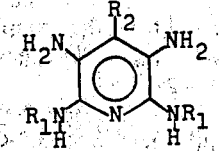

and

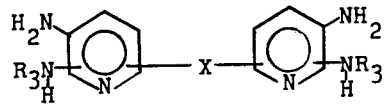

wherein $R_2$ represents a monovalent member selected from the group consisting of hydrogen, methyl, ethyl, propyl, butyl and pentyl;

$R_1$ represents a monovalent member selected from the group consisting of hydrogen, $C_1$-$C_5$ alkyl, substituted $C_1$-$C_5$ alkyl, $C_3$-$C_5$ alkenyl, phenyl, pyridyl, picolyl, quinolyl, substituted benzyl, and substituted phenyl, wherein the substituents on said members are selected from the group consisting of methyl, phenyl, pyridyl, -CN, -COOH and its salts,

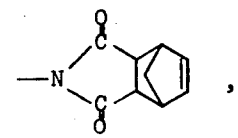

—$COOC_6H_5$, -$SO_3H$ and its salts, -SH, thioaryl, thioalkyl, —CH=$CHC_6H_5$, and N,N-dimethylamino; with the proviso that not all three of the $R_1$ and $R_2$ members can be H; and both of the $R_1$'s need not be identical;

$R_3$ is a monovalent radical selected from the group consisting of H and alkyl of 1 to 5 carbon atoms; and X is a covalent bond or a divalent radical selected from the group consisting of alkylene of 1 to 3 carbon atoms, -S-, -O-, and

where m is equal to 1 or 2; and each $R_3$NH- group is located ortho to an amino group and the pyridyl rings containing the amino groups are joined via the 2,2', 3,3', or 2,3' positions with the provisos that when X is a covalent bond both $R_3$'s cannot be hydrogen when the pyridyl groups are joined 2,2'; and when X is

the pyridyl groups are joined 2,2'; and further that both of the $R_3$'s need not be identical; and the acid salts thereof.

5. The compounds of claim 4 wherein the acid of said acid salts is selected from the group consisting of HCl, HBr, $H_3PO_4$, $H_2SO_4$, $CF_3COOH$, lower alkane sulfonic and perfluoroalkanesulfonic.

6. The process of claim 3 in which the reaction is carried out with a 2,6-di($R_6NH$)-4-$R_2$-3,5-dinitro-pyridine in the presence of an acid selected from alkanoic acids of two to five carbon atoms and the product is 2-(R''NH)-6-($R_6NH$)-4-$R_2$-3,5-dinitro-pyridine; $R_2$, $R_6$, and R'' are as defined in claim 4.

* * * * *